(12) United States Patent
Scopton

(10) Patent No.: US 7,811,250 B1
(45) Date of Patent: Oct. 12, 2010

(54) FLUID INJECTABLE SINGLE OPERATOR EXCHANGE CATHETERS AND METHODS OF USE

(75) Inventor: Paul M. Scopton, Winchester, MA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 1826 days.

(21) Appl. No.: 09/498,104

(22) Filed: Feb. 4, 2000

(51) Int. Cl.
A61M 29/00 (2006.01)
A61M 31/00 (2006.01)
A61M 37/00 (2006.01)
A61M 25/00 (2006.01)

(52) U.S. Cl. .............. 604/103.04; 604/96.01; 604/264; 604/523

(58) Field of Classification Search . 604/96.01–103.05, 604/165.02, 264, 523–528, 43; 606/192, 606/194
See application file for complete search history.

(56) References Cited

U.S. PATENT DOCUMENTS

| | | | |
|---|---|---|---|
| 1,204,053 A | 11/1916 | Moore | |
| 2,623,520 A | 12/1952 | Bamford, Jr. et al. | 128/221 |
| 3,015,869 A | 1/1962 | Rapata | 24/213 |
| 3,536,281 A | 10/1970 | Meehan et al. | 248/73 |
| 4,345,606 A | 8/1982 | Littleford | 128/784 |
| RE31,855 E | 3/1985 | Osborne | 604/161 |
| 4,696,668 A | 9/1987 | Wilcox | 604/28 |
| 4,748,982 A | 6/1988 | Horzewski et al. | 128/344 |
| 4,762,129 A | 8/1988 | Bonzel | 128/344 |
| 4,771,777 A * | 9/1988 | Horzewski et al. | 604/101.05 |
| 4,781,677 A | 11/1988 | Wilcox | 604/28 |
| 4,835,824 A | 6/1989 | Durham et al. | 24/339 |
| 4,844,092 A | 7/1989 | Rydell et al. | 128/772 |
| 4,900,184 A | 2/1990 | Cleveland | 403/397 |
| 4,905,667 A | 3/1990 | Foerster et al. | 128/4 |
| 4,917,103 A | 4/1990 | Gambale et al. | 128/772 |
| 4,927,418 A | 5/1990 | Dake et al. | 604/264 |
| 4,928,693 A | 5/1990 | Goodin et al. | 128/637 |

(Continued)

FOREIGN PATENT DOCUMENTS

DE 41 15 007 A1 11/1992

(Continued)

OTHER PUBLICATIONS

Knecht, Gregory L., M.D. et al., "Double-Channel Fistulotome for Endoscopic Drainage of Pancreatic Pseudocyst", *Gastrointestinal Endoscopy*, vol. 37, No. 3, May/Jun. 1991, pp. 356-357.

(Continued)

*Primary Examiner*—Matthew F Desanto
(74) *Attorney, Agent, or Firm*—Crompton, Seager & Tufte, LLC

(57) ABSTRACT

A single operator exchange biliary catheter having a tubular member extending proximally from the proximal guidewire port. The tubular member defines a guidewire lumen extension adapted to permit the guidewire to be retracted from guidewire lumen and re-inserted therein. By retracting the guidewire from the guidewire lumen and into the guidewire lumen extension, fluid may be readily injected via the guidewire lumen without encountering resistance to fluid flow from the guidewire. The guidewire lumen extension also maintains guidewire lumen access such that the guidewire may be easily re-inserted into the guidewire lumen.

9 Claims, 1 Drawing Sheet

U.S. PATENT DOCUMENTS

| | | | | |
|---|---|---|---|---|
| 4,932,413 | A | 6/1990 | Shockey et al. | 128/657 |
| 4,946,443 | A | 8/1990 | Hauser et al. | 604/165 |
| 4,983,168 | A | 1/1991 | Moorehead | 604/161 |
| 4,988,356 | A * | 1/1991 | Crittenden et al. | 604/96.01 |
| 4,997,421 | A | 3/1991 | Palsrok et al. | 604/174 |
| 5,040,548 | A | 8/1991 | Yock | 128/898 |
| 5,061,273 | A | 10/1991 | Yock | 606/194 |
| 5,064,414 | A | 11/1991 | Revane | 604/165 |
| 5,125,915 | A | 6/1992 | Berry et al. | 604/283 |
| 5,135,535 | A | 8/1992 | Kramer | 606/194 |
| 5,147,377 | A | 9/1992 | Sahota | 606/194 |
| 5,158,545 | A | 10/1992 | Trudell et al. | 604/53 |
| 5,167,634 | A | 12/1992 | Corrigan, Jr. et al. | 604/160 |
| 5,180,367 | A | 1/1993 | Kontos et al. | 604/101 |
| 5,195,978 | A | 3/1993 | Schiffer | 604/161 |
| 5,205,822 | A | 4/1993 | Johnson et al. | 604/96 |
| 5,219,335 | A * | 6/1993 | Willard et al. | 604/103.05 |
| 5,232,445 | A | 8/1993 | Bonzel | 604/96 |
| 5,248,306 | A | 9/1993 | Clark et al. | 604/283 |
| 5,250,033 | A | 10/1993 | Evans et al. | 604/160 |
| 5,263,932 | A | 11/1993 | Jang | 604/96 |
| 5,267,958 | A | 12/1993 | Buchbinder et al. | 604/96 |
| 5,279,562 | A | 1/1994 | Sirhan et al. | 604/96 |
| 5,281,203 | A * | 1/1994 | Ressemann | 604/164.13 |
| 5,282,479 | A | 2/1994 | Havran | 128/772 |
| 5,290,232 | A | 3/1994 | Johnson et al. | 604/96 |
| 5,290,241 | A | 3/1994 | Kraus et al. | 604/160 |
| 5,300,085 | A | 4/1994 | Yock | 606/191 |
| 5,306,247 | A | 4/1994 | Pfenninger | 604/96 |
| 5,308,318 | A | 5/1994 | Plassche, Jr. | 604/54 |
| 5,314,408 | A * | 5/1994 | Salmon et al. | 604/22 |
| 5,320,602 | A | 6/1994 | Karpiel | 604/54 |
| 5,324,259 | A | 6/1994 | Taylor et al. | 604/96 |
| 5,324,269 | A | 6/1994 | Miraki | 604/160 |
| 5,334,143 | A | 8/1994 | Carroll | 604/54 |
| 5,334,147 | A | 8/1994 | Johnson | 604/96 |
| 5,334,187 | A | 8/1994 | Fischell et al. | 604/194 |
| 5,336,184 | A | 8/1994 | Teirstein | 604/102 |
| 5,342,297 | A | 8/1994 | Jang | 604/53 |
| 5,350,395 | A | 9/1994 | Yock | 606/194 |
| 5,357,978 | A | 10/1994 | Turk | 128/772 |
| 5,364,355 | A | 11/1994 | Alden et al. | 604/96 |
| 5,364,376 | A | 11/1994 | Horzewski et al. | 604/280 |
| 5,368,567 | A | 11/1994 | Lee | 604/102 |
| 5,370,623 | A | 12/1994 | Kreamer | 604/165 |
| 5,380,283 | A | 1/1995 | Johnson | 604/96 |
| 5,387,226 | A | 2/1995 | Miraki | 606/194 |
| 5,389,087 | A | 2/1995 | Miraki | 604/247 |
| 5,395,335 | A | 3/1995 | Jang | 604/102 |
| 5,397,302 | A | 3/1995 | Weaver et al. | 604/54 |
| 5,409,459 | A | 4/1995 | Gambale | 604/96 |
| 5,413,559 | A | 5/1995 | Sirhan et al. | 604/102 |
| 5,415,639 | A | 5/1995 | VandenEinde et al. | 604/283 |
| 5,451,233 | A | 9/1995 | Yock | 606/194 |
| 5,454,790 | A | 10/1995 | Dubrul | 604/104 |
| 5,458,584 | A | 10/1995 | Ginn et al. | 604/280 |
| 5,458,605 | A | 10/1995 | Klemm | 606/108 |
| 5,462,530 | A | 10/1995 | Jang | 604/160 |
| 5,480,389 | A | 1/1996 | McWha et al. | 604/165 |
| 5,489,271 | A | 2/1996 | Andersen | 604/102 |
| 5,490,837 | A | 2/1996 | Blaeser et al. | 604/96 |
| 5,496,346 | A | 3/1996 | Horzewski et al. | 606/154 |
| 5,501,227 | A | 3/1996 | Yock | 128/662.06 |
| 5,531,700 | A * | 7/1996 | Moore et al. | 604/164.13 |
| 5,536,248 | A | 7/1996 | Weaver et al. | 604/54 |
| 5,540,236 | A | 7/1996 | Ginn | 128/772 |
| 5,599,299 | A | 2/1997 | Weaver et al. | 604/54 |
| 5,599,300 | A | 2/1997 | Weaver et al. | 604/54 |
| 5,626,600 | A | 5/1997 | Horzewski et al. | 606/194 |
| 5,706,827 | A | 1/1998 | Ehr et al. | 128/772 |
| 5,725,504 | A | 3/1998 | Collins | 604/165 |
| 5,788,681 | A | 8/1998 | Weaver et al. | 604/280 |
| 5,800,414 | A | 9/1998 | Cazal | 604/280 |
| 5,833,706 | A | 11/1998 | St. Germain et al. | 606/194 |
| 5,843,028 | A | 12/1998 | Weaver et al. | 604/54 |
| 5,849,016 | A | 12/1998 | Suhr | 606/108 |
| 5,921,971 | A | 7/1999 | Agro et al. | 604/280 |
| 5,984,945 | A * | 11/1999 | Sirhan | 606/194 |
| 6,007,522 | A | 12/1999 | Agro et al. | 604/264 |
| 6,096,009 | A | 8/2000 | Windheuser et al. | 604/165 |
| 6,152,910 | A | 11/2000 | Agro et al. | 604/523 |
| 6,190,358 | B1 * | 2/2001 | Fitzmaurice et al. | 604/102.02 |
| 6,322,577 | B1 * | 11/2001 | McInnes | 604/96.01 |
| 2001/0029362 | A1 * | 10/2001 | Sirhan et al. | 604/524 |

FOREIGN PATENT DOCUMENTS

| | | |
|---|---|---|
| EP | 0 328 760 A2 | 8/1989 |
| EP | 0 388 112 A2 | 9/1990 |
| EP | 0 792 657 A2 | 9/1997 |
| EP | 0 801 955 B1 | 10/1997 |
| WO | WO 92/03963 | 3/1992 |
| WO | WO 96/33764 | 10/1996 |
| WO | WO 98/10820 | 3/1998 |
| WO | WO 98/10821 | 3/1998 |
| WO | WO 99/38557 | 8/1999 |
| WO | WO 99/59664 | 11/1999 |
| WO | WO 00/64500 | 11/2000 |
| WO | WO 00/64900 | 11/2000 |

OTHER PUBLICATIONS

Siegel, Jerome H., M.D. et al., "Two New Methods for Selective Bile Duct Cannulation and Sphincterotomy", *Gastrointestinal Endoscopy*, vol. 33, No. 6, Dec. 1987, pp. 438-440.

Arndorfer Inc., Information Sheet, date unknown, 7 sheets.

* cited by examiner

FLUID INJECTABLE SINGLE OPERATOR EXCHANGE CATHETERS AND METHODS OF USE

CROSS REFERENCE TO RELATED APPLICATIONS

This application is related to U.S. patent application Ser. No. 09/312,340, filed on May 14, 1999, entitled "Single Operator Exchange Biliary Catheter with Common Distal Lumen"; which is a continuation-in-part application of U.S. patent application Ser. No. 09/080,520, filed on May 18, 1998, entitled "Guidewire and Catheter Locking Device and Method"; which is a continuation-in-part application of U.S. Pat. No. 6,007,522, issued on Dec. 28, 1999, entitled "Single Operator Exchange Biliary Catheter"; which claims priority to U.S. Provisional Application No. 60/025,235, filed Sep. 13, 1996, entitled "Single Operator Exchange Biliary Catheter", the entire disclosures of which are hereby incorporated by reference.

FIELD OF THE INVENTION

The present invention generally relates to endoscopic devices and methods of use. Specifically, the present invention relates to single operator exchange catheters for use in combination with guidewires and endoscopes.

BACKGROUND OF THE INVENTION

Endoscopic procedures for treating abnormal pathologies within the alimentary canal system and biliary tree (including the biliary, hepatic, and pancreatic ducts) are increasing in number. The endoscope provides access to the general area of a desired duct using direct visualization. However, the duct itself must be navigated using a catheter and guidewire in conjunction with fluoroscopy.

Catheters are generally known for treatment of targeted anatomical regions. For example, known biliary catheters and methods of use are disclosed in U.S. Pat. No. 5,397,302 to Weaver et al., and U.S. Pat. No. 5,320,602 to Karpiel, the disclosures of which are incorporated herein by reference. In general, for treatment of an abnormal pathology within a patient's biliary tree, an endoscope is first introduced into the mouth of the patient. The endoscope has a proximal end and a distal end, and includes a lumen extending longitudinally between the proximal and distal ends. The endoscope is guided through the patient's alimentary tract or canal until an opening at the distal end of the endoscope is proximate the area to receive treatment. At this point, the endoscope allows other components, such as a catheter, to access the targeted area.

For visualization and/or treatment within the biliary tree, the distal end of the endoscope is positioned proximate the papilla of vater leading to the common bile duct and the pancreatic duct. A catheter is guided through the lumen of the endoscope until a distal tip of the catheter emerges from the opening at the distal end of the endoscope. A guidewire may be used in conjunction with the catheter to facilitate accessing a desired location within the biliary tree. The guidewire is inserted into an opening at a proximal end of the catheter and guided through the catheter until it emerges from the distal end of the catheter. The catheter and guidewire are used to further access the biliary tree. The distal ends of the catheter and guidewire are guided through the orifice to the papilla of vater (located between the sphincter of oddi) leading to the common bile duct and the pancreatic duct.

For visualization and/or treatment of the common bile duct, the guidewire is guided into the common bile duct. The catheter is advanced over the guidewire or the catheter and guidewire are advanced together until the distal end of the catheter is positioned in the common bile duct at the desired location. The catheter is now in position for delivery of therapeutic agents or contrast media for fluoroscopic visualization of anatomical detail. Once the catheter and guidewire are in place relative to the targeted area, it is highly desirable to maintain position of the guidewire during subsequent catheter procedures, including catheter exchange procedures, so that re-navigating to the target site is unnecessary.

Present biliary endoscopic procedures utilize multi-lumen catheters for endoscopic retrograde cholangiopancreatography and endoscopic retrograde sphincterotomy, utilize balloon catheters for retrieval and stent delivery, and utilize other therapeutic and diagnostic devices. Conventional devices such as catheters used in these procedures are at least 200 cm long since they must pass through the endoscope, which is commonly at least 150 cm long. As described in general above, biliary endoscopic procedures are performed using a guidewire. Therefore, when using a standard catheter having a guidewire lumen extending the full length of the catheter, the guidewire must be at least 450 cm long to accommodate the exchange of different devices while maintaining access and position within the biliary tree. The exchange of devices over a 450 cm guidewire is both time consuming and cumbersome.

Due to the length of the guidewire, physicians require at least two assistants in the room to perform the procedure. Typically, one assistant is responsible for the patient and device-related concerns, while the other assistant is responsible for the guidewire. The additional hands required due to the length of the guidewire results in a relatively more time consuming and costly procedure.

To address these issues, single operator exchange catheters (also referred to as rapid exchange catheters) have been developed. An example a of single operator exchange catheter is disclosed in U.S. Pat. No. 6,007,522, issued on Dec. 28, 1999, entitled "Single Operator Exchange Biliary Catheter", the entire disclosure of which is incorporated herein by reference. Such single operator exchange catheters are adapted for use within the alimentary canal and have features which facilitate rapid exchange and allow an exchange procedure to be performed by a single operator. Specifically, single operator exchange catheters may be used in connection with a conventional length guidewire, and thus are easier to use and require less personnel for performing biliary procedures.

Single operator exchange catheters have a relatively short distal guidewire lumen extending between a distal guidewire port disposed adjacent the distal end of the catheter and a proximal guidewire port disposed distal of the proximal end of the catheter and proximal of the distal end of the catheter. The guidewire extends through the guidewire lumen between the proximal and distal guidewire ports.

SUMMARY OF THE INVENTION

Some types of single operator exchange catheters have an injection lumen in fluid communication with the guidewire lumen. An example of this type of catheter is disclosed in U.S. patent application Ser. No. 09/312,340, filed on May 14, 1999, entitled "Single Operator Exchange Biliary Catheter with Common Distal Lumen", the entire disclosure of which is hereby incorporated by reference. With this type of single operator exchange catheter, the injection lumen extends from an injection port or connector disposed at the proximal end of the catheter to allow for the injection of fluids therein. Fluid injected into the injection port flows through the injection lumen, into the guidewire lumen, and out the distal guidewire port. This may be used to aid visualization by injecting contrast media or for other purposes such as the injection of therapeutic agents.

Unfortunately, for a number of reasons, single operator exchange catheters that utilize the guidewire lumen for fluid delivery may not be well suited for fluid injection. First, fluid may tend to leak out of the proximal guidewire port, even with the guidewire disposed therein. Second, significant resistance to flow (i.e., drag) may be encountered in the guidewire lumen due to the presence of the guidewire which reduces the cross-sectional area available for fluid flow. Third, retracting the guidewire in the proximal direction in order to reduce flow resistance in the guidewire lumen may risk the loss of access to the guidewire lumen. Re-insertion of the guidewire into the proximal guidewire port may be difficult, if not impossible, without completely removing the catheter and guidewire from the patient. Adding an additional lumen for fluid delivery is not an ideal solution because it increases the profile of the catheter, which is undesirable because the catheter may not be as easily navigated and the catheter may take up excessive space in the lumen of the endoscope. As such, it is desirable to provide a single operator exchange catheter that more effectively provides for fluid injection via the guidewire lumen.

The present invention provides a single operator exchange biliary catheter, such as a balloon catheter, having a tubular member disposed adjacent the proximal guidewire port. The tubular member defines a guidewire lumen extension adapted to permit the guidewire to be retracted from guidewire lumen for fluid injection. After fluid delivery, the guidewire may be re-inserted into the guidewire lumen. By retracting the guidewire from the guidewire lumen and into the guidewire lumen extension, fluid may be readily injected via the guidewire lumen without encountering resistance to flow from the guidewire. In addition, the guidewire lumen extension maintains access to the guidewire lumen such that the guidewire may be easily re-inserted into the guidewire lumen.

In an exemplary embodiment, the present invention provides a biliary catheter for use in combination with a guidewire and an endoscope. The biliary catheter includes an elongate shaft having an injection lumen extending therethrough. A guidewire lumen extends through a distal portion of the shaft between a proximal guidewire port and a distal guidewire port. The guidewire lumen is in fluid communication with the injection lumen of the shaft. A tubular member is connected to the shaft, preferably adjacent the proximal guidewire port. The tubular member has a proximal end disposed distal of the proximal end of the shaft, and a distal end disposed adjacent to or distal of the proximal guidewire port. The tubular member defines a guidewire lumen extension adapted to permit the guidewire to be retracted from guidewire lumen and re-inserted therein.

The tubular member may be disposed about the shaft, with the distal end of the tubular member fluidly sealed about the proximal guidewire port or about the shaft distal of the proximal guidewire port. The proximal end of the guidewire lumen extension may be sized to restrict flow about the guidewire. By sealing the distal end of the tubular member and sizing the proximal end of the guidewire lumen extension to restrict flow about the guidewire, leakage via the proximal guidewire port is minimized during fluid injection.

The guidewire lumen extension of the tubular member may be axially aligned with the guidewire lumen to minimize guidewire friction. To accomplish this, the shaft of the catheter may be radially shifted at the proximal guidewire port such that the guidewire remains substantially straight therethrough.

Although specifically described hereinafter as a heat shrink tube having a length of approximately 5-30 cm, the tubular member may be manifested in a wide variety of forms that serve the same or similar functions. These functions include allowing retraction of the guidewire from the guidewire lumen, maintaining access to the guidewire lumen, and preferably minimizing leakage during fluid injection. Thus, for example, the tubular member and the shaft adjacent the tubular member may be replaced with a multi-lumen tube welded therein. Alternatively, the tubular member may comprise a simple retaining structure such as a loop, clip, or the like in combination with a gasket-type seal. Those skilled in the art will recognize that other suitable structures may be used to serve the same or similar functions.

In another exemplary embodiment, the present invention provides a method of using a biliary catheter. After the endoscope has been inserted into the patient, a single operator exchange catheter substantially as described previously is inserted into the endoscope over a guidewire. At any point during the procedure, particularly when it is desirable to inject fluid through the catheter, the guidewire may be retracted from guidewire lumen until the guidewire resides in the guidewire lumen extension of the tubular member. Fluid may then be injected into the injection lumen of the catheter, through the guidewire lumen and out the distal guidewire port. After injection is complete, the guidewire may be re-inserted into the guidewire lumen via the proximal guidewire port.

DETAILED DESCRIPTION OF THE INVENTION

The following detailed description should be read with reference to the drawings in which similar elements in different drawings are numbered the same. The drawings, which are not necessarily to scale, depict selected preferred embodiments and are not intended to limit the scope or spirit of the invention.

Figure 1:
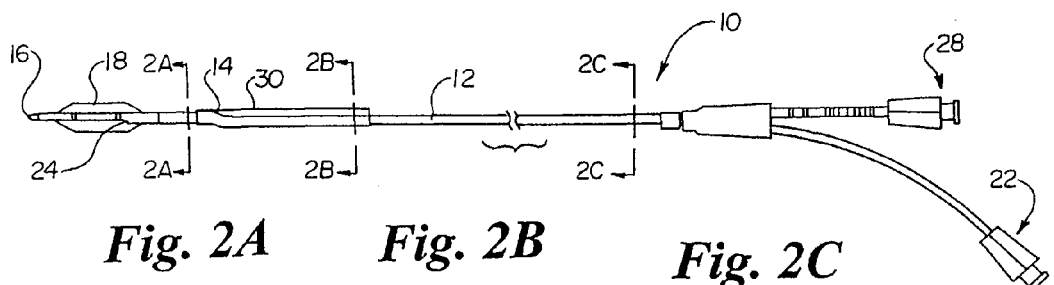
FIG. 1 is a perspective view of a single operator exchange catheter in accordance with the present invention.

Refer now to FIG. 1 which illustrates a perspective view of a single operator exchange catheter 10 in accordance with the present invention. For purposes of illustration only, the single operator exchange catheter 10 of the present invention is shown and described as a balloon catheter. Those skilled in the art will readily appreciate that the single operator exchange catheter 10 may comprise almost any form of catheter including a balloon catheter as shown, a multi-lumen catheter, or the like. For purposes of discussion, the present invention is described with reference to a single operator exchange balloon catheter 10 as shown in FIG. 1, but is not limited to such.

Except as described herein, the single operator exchange catheter 10 may have the same or similar features, materials and dimensions as the single operator exchange catheter disclosed in co-pending U.S. patent application Ser. No. 09/312,340, filed May 14, 1999 entitled "Single Operator Exchange Biliary Catheter with Common Distal Lumen", the entire disclosure of which is incorporated herein by reference.

Figure 2A:
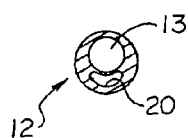
FIG. 2A is a cross-sectional view of the catheter of FIG. 1 taken along line 2A-2A.

Single operator exchange balloon catheter 10 includes an elongate shaft 12 having a distal guidewire lumen 13 as best seen in FIG. 2A. The guidewire lumen 13 extends between a proximal guidewire port 14 and a distal guidewire port 16. The proximal guidewire port 14 is disposed distal of the proximal end of the elongate shaft 12 and proximal of the distal end of the elongate shaft 12. Distal guidewire port 16 is disposed at or near the distal end of the elongate shaft 12.

Figure 2B:
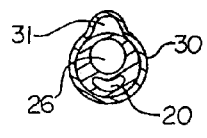
FIG. 2B is a cross-sectional view of the catheter of FIG. 1 taken along line 2B-2B.
Figure 2C:
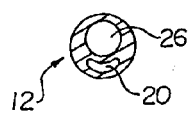
FIG. 2C is a cross-sectional view of the catheter of FIG. 1 taken along line 2C-2C.

An inflatable balloon 18 is disposed adjacent the distal end of the elongate shaft 12. The inflatable balloon 18 is in fluid communication with an inflation lumen 20 as best seen in FIGS. 2A-2C. The inflation lumen 20 extends from a proximal inflation port 22 through the elongate shaft 12 and terminates at an inflation lumen opening 24 disposed within the balloon 18. With this arrangement, the balloon 18 may be inflated and deflated by connecting a suitable inflation device, syringe or similar device to the inflation port 22.

As best seen in FIG. 2C, the elongate shaft 12 also defines an injection lumen 26 extending from a proximal injection port 28 through the elongate shaft 12 to the proximal guidewire port 14. The injection lumen 26 is in fluid communication with the distal guidewire lumen 13. With this arrangement, fluid may be injected by connecting a syringe or similar device to the injection port 28 and injecting fluid through the injection lumen 26 into the guidewire lumen 13 and out the distal guidewire port 16.

A stiffening stylet (not shown) may be inserted into the injection lumen 26 to provide enhanced pushability of the elongate shaft 12. The diameter of such a stylet may approximate the inside diameter of the injection lumen 26. Alternatively, to avoid the necessity of withdrawing such a stylet for fluid injection, the stylet may be smaller than the inside diameter of the injection lumen 26 to provide sufficient annular space to allow fluid to flow therethrough. Alternatively, the stiffening stylet may be replaced with a hollow tubular member such as a stainless steel hypotube to allow for fluid flow therethrough.

Figure 3:
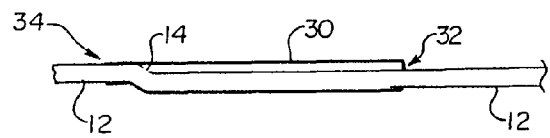
FIG. 3 is a fragmentary perspective view of a portion of the single operator exchange catheter illustrated in FIG. 1.

A significant difference between the single operator exchange catheter 10 of the present invention and the prior art is the provision of a tubular member 30. As best seen with reference to FIG. 3, tubular member 30 is connected to the elongate shaft 12 and extends proximally from the proximal guidewire port 14. The tubular member 30 has a proximal end 32 disposed distal of the proximal end of the elongate shaft 12 and proximal of the proximal guidewire port 14. The proximal end 32 of the tubular member 30 defines an opening sized to accommodate a guidewire therein. The tubular member 30 also includes a distal end 34 disposed adjacent to or distal of the proximal guidewire port 14. The distal end 34 of the tubular member 30 forms a seal about the proximal guidewire port 14. Preferably, the distal end 34 sealingly surrounds the elongate shaft 12 immediately distal of the proximal guidewire port 14.

As best seen in FIG. 2B, the tubular member 30 defines a guidewire lumen extension 31 extending therethrough, which is in fluid communication with the guidewire lumen 13 of the elongate shaft 12. The guidewire lumen extension 31 of the tubular member 30 is axially aligned with the guidewire lumen of the elongate shaft 12 such that guidewire friction is minimized. To provide such axial alignment, the elongate shaft may be radially shifted at the proximal guidewire port 14. Although the guidewire lumen extension 31 is axially aligned with the guidewire lumen 13, it may be desirable to provide a directing means such as a loading ramp located adjacent the proximal guidewire port 14 to assure that a backloaded guidewire enters into the guidewire lumen extension 31 and not into the injection lumen 26 of the elongate shaft 12.

Figure 4A:
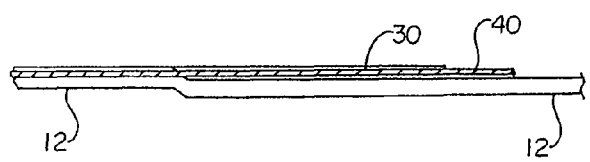
FIG. 4A is a fragmentary perspective view as in FIG. 3, with a guidewire extending through the guidewire lumen of the single operator exchange catheter.
Figure 4B:
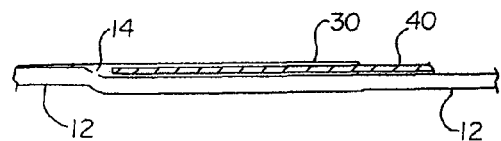
FIG. 4B is a fragmentary perspective view as in FIG. 3, with a guidewire retracted from the guidewire lumen of the single operator exchange catheter.

With the guidewire lumen extension 31 in axial alignment with the guidewire lumen 13 of the shaft 12, the guidewire 40 remains substantially straight through the proximal guidewire port 14 thereby minimizing guidewire friction, as best seen in FIG. 4A. With this arrangement, the guidewire 40 may be easily retracted in the proximal direction such that the distal end of the guidewire 40 is removed from the guidewire lumen 13 to reside within the guidewire lumen extension 31 as best seen in FIG. 4B. Also with this arrangement, the guidewire 40 may be readily re-inserted into the guidewire lumen of the elongate shaft 12 through the guidewire port 14 simply by advancing the guidewire 40 in the distal direction.

As mentioned above, the distal end 34 of the tubular member 30 sealingly surrounds the elongate shaft 12. The proximal end 32 of the tubular member 30 limits the egress of fluid therethrough by closely approximating the inside diameter of the guidewire lumen extension 31 to the outside diameter of the guidewire 40. By sealing the distal end 34 of the tubular member 30 and sizing the proximal end 32 of the guidewire lumen extension 31 to restrict flow about the guidewire 40, leakage via the proximal guidewire port 14 is minimized during fluid injection.

The tubular member 30 may be constructed of any suitable polymer, but preferably comprises a heat shrink tubing having a length ranging from approximately 5 cm to 30 cm. The tubular member 30 in its initial state may be slid over the distal end of the elongate shaft 12 until the distal end 34 is positioned immediately distal of and adjacent to the proximal guidewire port 14. A mandrel may then be inserted into the guidewire lumen extension 31, through the proximal guidewire port 14, and into the guidewire lumen 13. The mandrel serves to maintain alignment between the tubular member 30 and the elongate shaft 12 such that the guidewire lumen extension 31 is axially aligned with the guidewire lumen 13. The mandrel preferably has an outside diameter approximately equal to or slightly greater than the nominal diameter of the guidewire 40. This provides a close fit between the inside surface of the tubular member 30 and the guidewire 40 such that the egress of fluid therebetween is minimized during fluid injection. With the tubular member 30 in the desired position, heat is applied along the tubular member 30 to shrink the tube 30 about the shaft 12 and mandrel such that the tube 30 conforms thereto. The distal end 34 of the tubular member may be sealed about the elongate shaft 12 utilizing thermal welding or a suitable adhesive. The proximal end 32 of the tubular member 30 may be adhesively or thermally connected to the elongate shaft 12 opposite the guidewire lumen extension 31. Alternatively, it may suffice to rely on the mechanical connection established by heat shrinking the tubular member 30 about the elongate shaft 12. After the tubular member is secured to the shaft 12, the mandrel may be removed.

Those skilled in the art will recognize that other suitable structures may be used in place of tubular member 30 to serve the same or similar functions. These functions include allowing retraction of the guidewire 40 from the guidewire lumen 13; maintaining access to the guidewire lumen 13; and preferably minimizing leakage during injection. For example, the elongate shaft 12 in the region of the tubular member 30 may be replaced with a multi-lumen extrusion welded therein. The multi-lumen extrusion would define the lumens 20, 26 of the elongate shaft 12 in addition to the guidewire lumen extension 31 previously defined by the tubular member 30. Alternatively, the tubular member 30 may be replaced by a simple retaining structure such as a loop, clip or the like in combination with a gasket type seal that forms a fluid seal about the guidewire.

In use, the endoscope (not shown) is first introduced into the mouth of the patient and is guided through the patient's alimentary canal. Specifically, the endoscope is guided down the esophagus, through the stomach, past the pyloric sphincter of the stomach and into the duodenum. The endoscope is guided through the alimentary canal until its distal end is adjacent the target site. In an endoscopic biliary procedure, the endoscope is guided into the duodenum until the distal end of the endoscope is proximate the papilla of vater. The papilla of vater is located between the sphincter of oddi which leads to the common bile duct, the hepatic duct and the pancreatic duct. The proximal end of the endoscope remains outside the mouth of the patient to facilitate manipulation of the endoscope and insertion of catheters and guidewires into the endoscope.

With the endoscope properly positioned within the patient, the catheter 10 is prepared for insertion into the endoscope. First, the guidewire 40 may be fed into the guidewire lumen 13 utilizing a backloading technique. Specifically, the proximal end of the guidewire 40 is inserted into the distal guidewire port 16 and advanced in a proximal direction until the guidewire exits the proximal guidewire port 14, passes through the guidewire lumen extension 31 and exits through the proximal end 32 of the tubular member 30. The catheter 10 is then advanced along the guidewire 40 until the distal end of the catheter 10 is adjacent the distal end of the guidewire 40. The catheter 10 and guidewire 40 are then inserted into the endoscope and advanced to the distal end thereof. The catheter 10 and the guidewire 40 may be advanced in unison or may be advanced and navigated individually until the distal end of the catheter 10 is adjacent the desired target site in the biliary tree (including the common bile, hepatic or pancreatic ducts).

At any point during the procedure, particularly when it is desirable to inject fluid through the catheter 10, the guidewire 40 may be retracted from the guidewire lumen 13 until the distal end of the guidewire 40 resides within the guidewire lumen extension 31 of the tubular member 30. With the guidewire 40 positioned within the guidewire lumen extension 31, the proximal guidewire port 14 is effectively sealed by virtue of the fluid sealed ends of the tubular member 30. Specifically, as mentioned previously, the distal end 34 of the tubular member 30 is sealed about the elongate shaft 12, and the proximal end 32 of the guidewire lumen extension 31 is sized to inhibit the egress of fluid therethrough when the guidewire 40 is positioned therein. Thus, a sealed fluid path is defined across the proximal guidewire port 14 between the injection lumen 26 and the guidewire lumen 13.

With this arrangement, fluid may be injected into the injection lumen 26, past the proximal guidewire port 14, through the guidewire lumen 13 and out the distal guidewire port 16. After the injection of fluid is complete, the guidewire 40 may be advanced in the distal direction such that the distal end of the guidewire 40 is re-inserted into the guidewire lumen 13 of the elongate shaft 12. After the desired procedure has been completed, the catheter 10 may be exchanged or removed from the endoscope, leaving the guidewire 40 in position for other catheter procedures.

From the foregoing, it is apparent that the single operator exchange catheter 10 of the present invention provides a number of advantages over prior art catheters by incorporating a tubular member 30 disposed adjacent the proximal guidewire port 14. The tubular member 30 defines a guidewire lumen extension 31 adapted to permit the guidewire 40 to be retracted from the guidewire lumen 13 and re-inserted therein. By retracting the distal end of the guidewire 40 from the guidewire lumen 13 and into the guidewire lumen extension 31, fluid may be readily injected through the guidewire lumen 13 without encountering resistance to flow from the guidewire 40. The guidewire lumen extension 31 of the tubular member 30 also maintains guidewire lumen 13 access such that the guidewire 40 may be readily re-inserted into the guidewire lumen 13.

By providing such a catheter 10, the present invention overcomes the potential disadvantages of single operator exchange catheters that utilize the guidewire lumen for fluid delivery, as discussed previously. Specifically, the catheter 10 of the present invention eliminates fluid leaks through the proximal guidewire port 14, reduces or eliminates resistance to flow through the guidewire lumen 13 and reduces if not eliminates the risk of losing access to the guidewire lumen 13 when the guidewire 40 is retracted in the proximal direction. All of these features are provided without the need for an additional injection lumen.

Those skilled in the art will recognize that the present invention may be manifested in a wide variety of forms other than the specific embodiments contemplated and described herein. Accordingly, departures in form and detail may be made without departing from the scope and spirit of the present invention as described in the appended claims.

What is claimed is:

1. A single operator exchange biliary catheter for use in combination with a guidewire and an endoscope, comprising:
   an elongate shaft having a proximal end, a distal end and an injection lumen extending therethrough;
   a guidewire lumen extending through a distal portion of the shaft between a proximal guidewire ort and a distal guidewire port, the guidewire lumen being in fluid communication with the injection lumen of the shaft, the proximal guidewire port disposed proximal of the distal end of the shaft within the distal portion of the shaft, the distal guidewire port disposed at the distal end of the shaft;
   a tubular member connected to the shaft, the tubular member extending proximally from the proximal guidewire port to a proximal end disposed distal of the proximal end of the shaft, the tubular member defining a guidewire lumen extension in fluid communication with the guidewire lumen and adapted to permit the guidewire to be retracted from guidewire lumen and re-inserted therein, the guidewire lumen extension being external to but parallel with the shaft;
   wherein the guidewire lumen extension is axially aligned with the guidewire lumen; and
   wherein the tubular member has a length of approximately 5 to 30 cm.

2. A biliary catheter as in claim 1, wherein the tubular member comprises a heat shrink tube.

3. A single operator exchange biliary balloon catheter for use in combination with a guidewire and an endoscope, comprising:

an elongate shaft having a proximal end, a distal end, an injection lumen and an inflation lumen extending therethrough;

an inflatable balloon disposed adjacent the distal end of the shaft in fluid communication with the inflation lumen;

a guidewire lumen extending through a distal portion of the shaft between a proximal guidewire port and a distal guidewire port, the guidewire lumen being in fluid communication with the injection lumen of the shaft, the proximal guidewire port disposed proximal of the distal end of the shaft within the distal portion of the shaft, the distal guidewire port disposed at the distal end of the shaft; and a tubular member disposed about the shaft, the tubular member having a proximal end disposed distal of the proximal end of the shaft, and a distal end disposed distal of the proximal guidewire port, the tubular member defining a guidewire lumen extension in fluid communication with the guidewire lumen and adapted to permit the guidewire to be retracted from guidewire lumen and re-inserted therein, the guidewire extension lumen being external to but parallel with the shaft;

wherein the guidewire lumen extension is axially aligned with the guidewire lumen.

4. A single operator exchange biliary balloon catheter as in claim 3, wherein the distal end of the tubular member is disposed adjacent the proximal guidewire port.

5. A single operator exchange biliary balloon catheter as in claim 4, wherein the distal end of the tubular member is fluidly sealed about the shaft.

6. A single operator exchange biliary balloon catheter as in claim 5, wherein a proximal portion of the guidewire lumen extension is sized to restrict flow about the guidewire disposed therein.

7. A single operator exchange biliary balloon catheter as in claim 3, wherein the tubular member has a length of approximately 5 to 30 cm.

8. A single operator exchange biliary balloon catheter as in claim 7, wherein the tubular member comprises a heat shrink tube.

9. A single operator exchange biliary balloon catheter as in claim 3, wherein the shaft of the catheter is radially shifted at the proximal guidewire port such that the guidewire may remain substantially straight through the proximal guidewire port.

\* \* \* \* \*